(12) United States Patent
Hartwick

(10) Patent No.: US 7,530,946 B2
(45) Date of Patent: May 12, 2009

(54) COMPACT ENDOSCOPE

(75) Inventor: Darrell J. Hartwick, Newton, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 118 days.

(21) Appl. No.: 10/641,065

(22) Filed: Aug. 15, 2003

(65) Prior Publication Data
US 2005/0038320 A1 Feb. 17, 2005

(51) Int. Cl.
*A61B 1/00* (2006.01)
*A61B 1/04* (2006.01)
*A61B 1/06* (2006.01)

(52) U.S. Cl. .................. 600/160; 600/110; 600/130

(58) Field of Classification Search ............. 600/109, 600/110, 130, 134, 160, 182
See application file for complete search history.

(56) References Cited

U.S. PATENT DOCUMENTS

| | | | |
|---|---|---|---|
| 4,616,631 A | 10/1986 | Takahashi | |
| 4,773,396 A | 9/1988 | Okazaki | |
| 4,832,023 A | 5/1989 | Murphy-Chutorian et al. | |
| 5,178,616 A | 1/1993 | Uemiya et al. | |
| 5,259,366 A | 11/1993 | Reydel et al. | |
| 5,311,007 A * | 5/1994 | Kato | 250/208.1 |
| 5,569,158 A | 10/1996 | Suzuki et al. | |
| 5,575,757 A | 11/1996 | Kennedy et al. | |
| 5,704,892 A * | 1/1998 | Adair | 600/121 |
| 5,873,816 A * | 2/1999 | Kagawa et al. | 600/134 |
| 5,876,331 A | 3/1999 | Wu et al. | |
| 6,139,489 A | 10/2000 | Wampler et al. | |
| 6,142,930 A | 11/2000 | Ito et al. | |
| 6,165,123 A * | 12/2000 | Thompson | 600/152 |
| 6,293,910 B1 | 9/2001 | Yamakita et al. | |
| 6,319,197 B1 * | 11/2001 | Tsuji et al. | 600/132 |
| 6,509,521 B1 | 1/2003 | Geitz | |

* cited by examiner

*Primary Examiner*—John P. Leubecker
*Assistant Examiner*—Philip R Smith
(74) *Attorney, Agent, or Firm*—Fulbright & Jaworski L.L.P.

(57) ABSTRACT

This invention relates to an endoscope, particularly a bronchoscope, incorporating one or more multifunctional component made of a material that is multifunctional. The endoscopes of this invention comprise at least one multifunctional component having more than one function wherein the functions were previously performed separately by individual components.

23 Claims, 4 Drawing Sheets

US 7,530,946 B2

COMPACT ENDOSCOPE

FIELD OF THE INVENTION

This invention relates to an endoscope, particularly a video bronchoscope, incorporating one or more multifunctional components.

BACKGROUND OF THE INVENTION

Generally endoscopes are instruments for visualizing the interior of a human body and typically comprise a flexible or rigid outer tube having a lens at the distal end of the tube. Positioned within the tube are steering components and other components that transmit a signal to and from the lens. One of the disadvantages of currently available endoscopes is their expense, which is due in part to the extensive hand labor involved in their construction by the serial assembly of numerous small components. The cost of each of the numerous components wherein each component has a single function, also contributes to the expense of the endoscopes which in turn effectively reduces the feasibility of discarding the endoscope after a single use. Because the endoscopes are not disposable, they must be made of a material that withstands repeated cleanings and must be sealed so that unwanted materials are not transferred from one patient to another. While reusable endoscopes are currently available, they require frequent costly repairs and are expensive to clean and maintain.

Another disadvantage of currently available endoscopes is their relatively large size, which limits access to particular areas in a patient and contributes to the physical discomfort experienced by a patient during manipulation of the endoscope. Although efforts to reduce endoscope size have been made, they have met with limited success. Therefore it would be desirable to design smaller endoscopes, which may also be produced inexpensively, so that it would be economically feasible to have "disposable" endoscopes, which could be used once and then discarded.

Efforts have been made to produce small endoscopes economically. See for example, U.S. Pat. No. 4,773,396 issued Sep. 27, 1988, U.S. Pat. No. 5,575,757 issued Nov. 19, 1996 and U.S. Pat. No. 6,293,910 issued Sep. 25, 2001. In each of these patents endoscopes are described that contain various components, each having a single distinct function.

SUMMARY OF THE INVENTION

The endoscopes described herein are designed so that various components are made of materials that are multifunctional and thus reduces the number of components, consequently reducing overall endoscope size. The use of such multifunctional materials also results in a reduction in labor costs associated with endoscope production and thus an overall reduction in cost of the finished product. By reducing their cost, the endoscopes can be economically produced making it feasible to discard the endoscope after a single use.

This invention relates to an endoscope, particularly a bronchoscope, incorporating one or more multifunctional components made of a material which is multifunctional, such components are referred to hereinafter as "multifunctional components." U.S. Pat. No. 4,832,023 describes a catheter comprising an element composed of a glass fiber core surrounded by a coiled wire sheath. The sheath is spaced radially outwardly from the core by a series of insulative annular spacers. The glass fiber core transmits a laser signal and the wire sheath provides flexibility and mobility. This catheter element differs from the multifunctional components in the endoscopes of this invention in that the catheter element is composed of multiple materials, i.e., the glass fiber core and coiled wire sheath, each having its own function: In contrast, each multifunctional components of this invention are made of a material that serves more than one function.

The endoscopes of this invention comprise at least one multifunctional component having more than one function wherein the functions were previously performed separately by individual components. Incorporating more than one function into a single component allows for the construction of small endoscopes suitable for small spaces e.g., insertion into smaller body lumens, and a reduction in the discomfort a patient experiences while undergoing an endoscopic procedure. In addition, because the number of components is reduced, so is the labor involved in endoscope construction and ultimately the cost of the finished product. Furthermore, by reducing their cost, it is feasible to use the endoscopes once and then discard them. By eliminating the need to re-use the endoscope, one reduces the incidence of transferring an undesirable material, e.g., infectious material, from one patient to another. Furthermore, endoscopes that are used more than once must be reprocessed prior to a second use. Thus they must be made watertight to prevent leakage during repeated immersions in liquid and also be made of a material that withstands repeated cleaning. Thus an additional advantage of the disposable endoscopes of this invention is that they do not need to be completely sealed and do not need to be made of materials that are reprocessable, e.g., resistant to cleaning solutions and high heat.

In addition to being used for visualizing the interior of a human body, the endoscopes of this invention may also be used to deliver a substance through the lumen of the endoscope tube to a subject in need thereof. For example, any suitable gas, liquid, gel or powder, e.g., cyanoacrylate adhesive, may be administered through the lumen. Preferably the substance is a pharmaceutically acceptable substance. Therapeutic materials, e.g., an antibiotic, a mycostatic material, or an antineoplastic material, could be delivered to a subject in need thereof by using the endoscopes of this invention. Open lumens within the endoscopes may also be used to facilitate the insertion of instruments into a patient.

DETAILED DESCRIPTION OF THE INVENTION

Figure 1A:
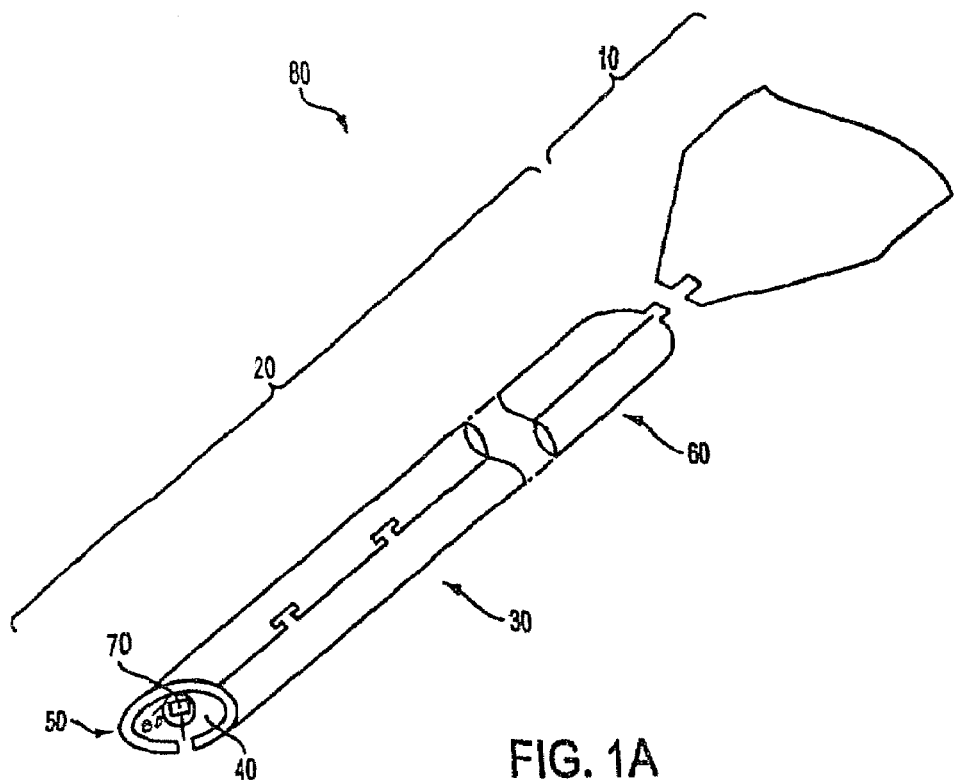
FIG. 1A depicts an endoscope with a proximal (10) and distal (20) portion, a tube (30) with an open lumen (40) and an electronic chip (70).
Figure 1B:
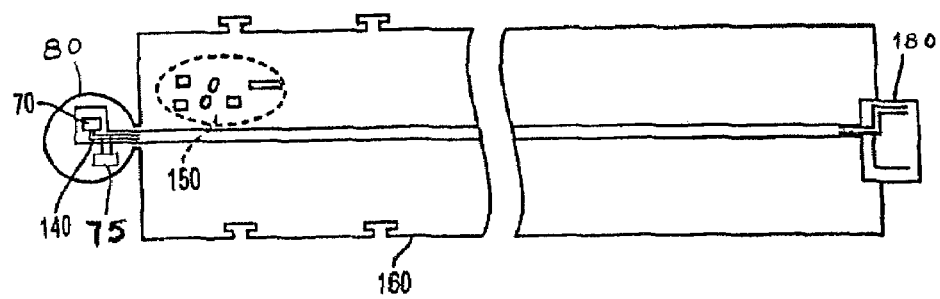
FIG. 1B depicts a flattened flex circuit (160) with an electronic chip (70) attached by wires (140) to the flex circuit and signal processing components (150) attached to the flex circuit.
Figure 2:
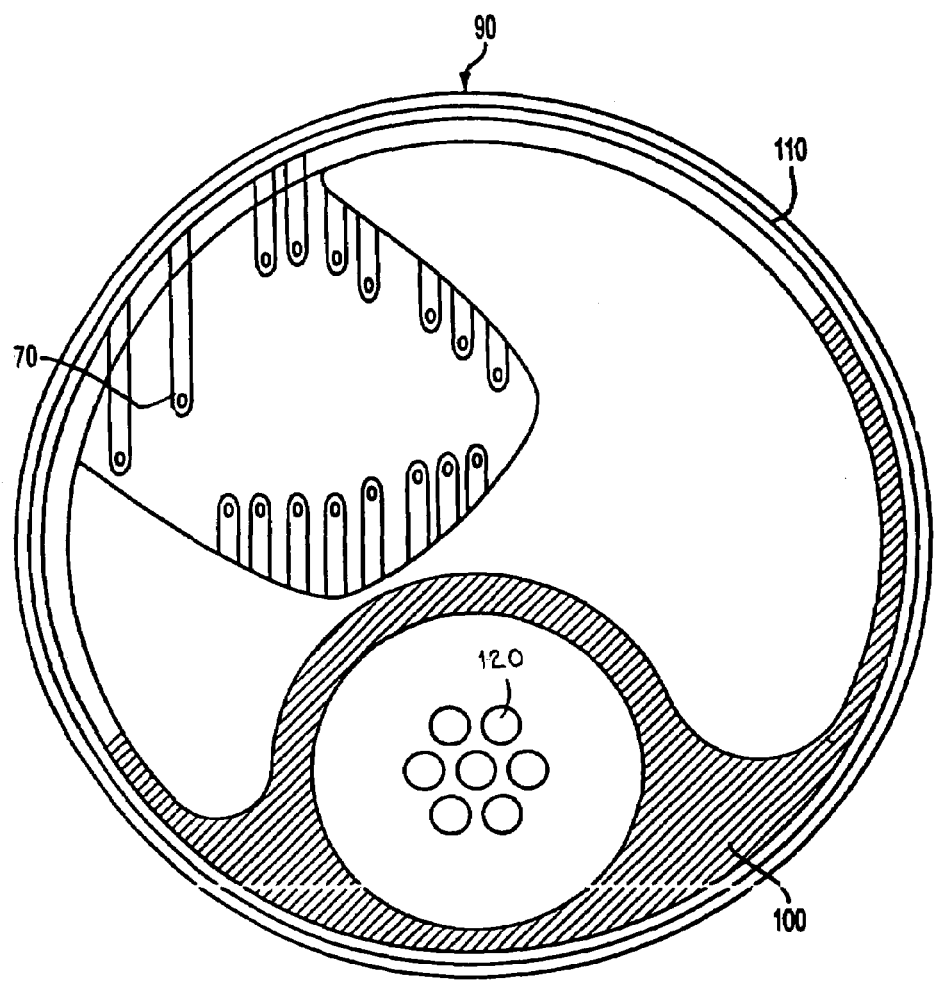
FIG. 2 is a cross section of an endoscope depicting the shielding (90), compressive (100) and conductive (110) layers and an electronic chip (70).
Figure 3:
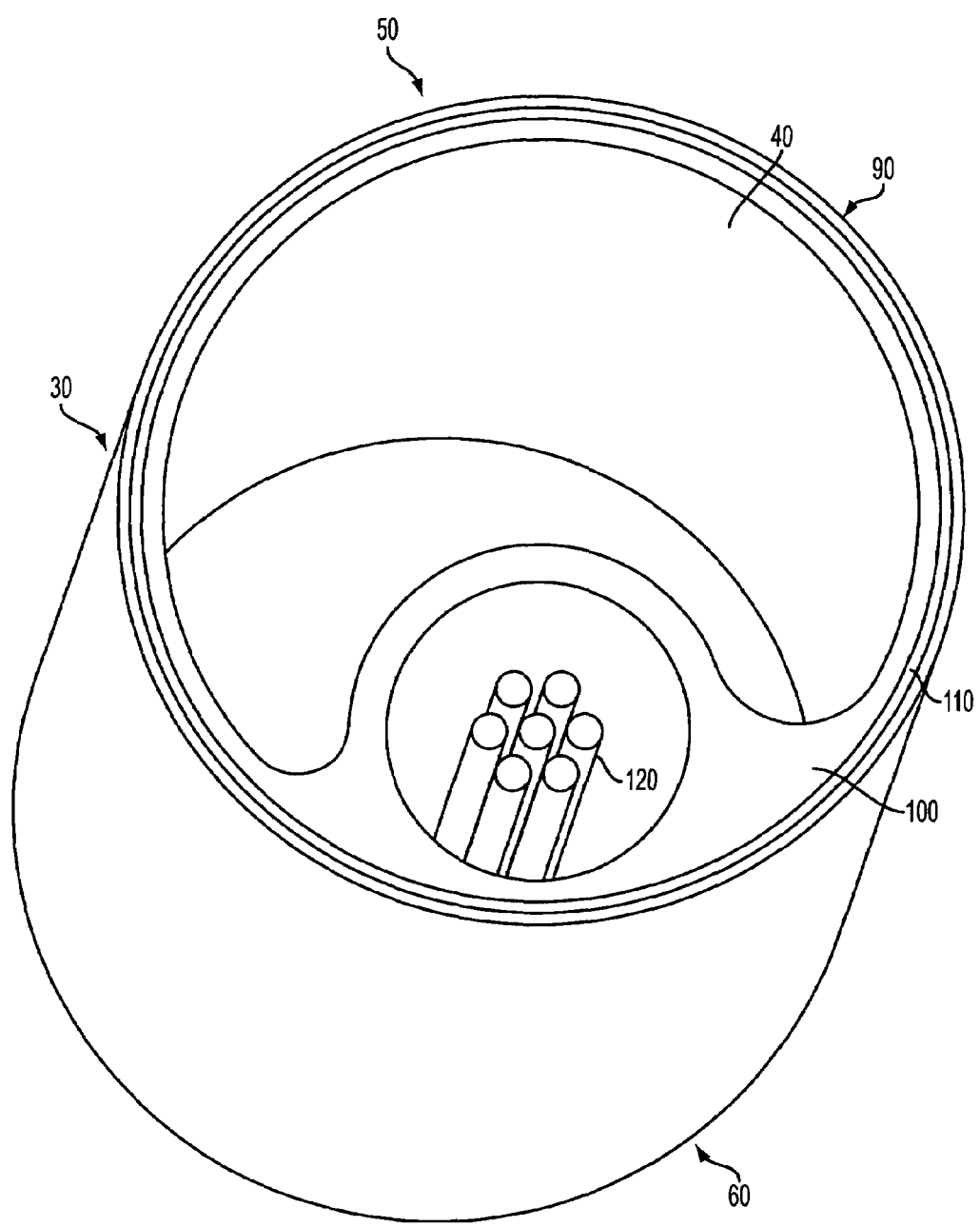
FIG. 3 is a cross section of an endoscope depicting the proximal end (50) and the distal end (60) of the endoscope tube (30), the shielding (90), compressive (100) and conductive (110) layers, and a plurality of tensile members (120).

The endoscopes of this invention have a proximal portion (10) and a distal portion (20), wherein the distal portion (20) comprises a tube (30) having an open lumen (40) and wherein the tube has a distal end (50) and a proximal end (60), an electronic chip (70) and a lens (80) as shown in FIG. 1. The tube comprises an outer shielding layer or sheath layer (90), an inner compressive layer (100) and a middle conductive layer (110) as shown in FIG. 2. The endoscope also comprises a plurality of tensile members (120) which extend from the distal end (50) to proximal end (60) of the tube (30) and may be positioned such that the tensile members (120) are surrounded by the compressive layer (100) (see e.g., FIGS. 1-3). The endoscopes described herein differ from those previously described by comprising components that have multiple functions, e.g., two or more functions of light transmission, current transmission, or load bearing properties. For example, one or more of the layers of the endoscope tube may be made of a material that also transmits light, e.g., any or all of the outer, middle or inner layers may transmit light, in addition to providing shielding (outer layer), signals/current (middle conductive layer), or load bearing (inner compressive layer). Described herein are endoscopes comprising various combinations of multifunctional components.

Figure 4:
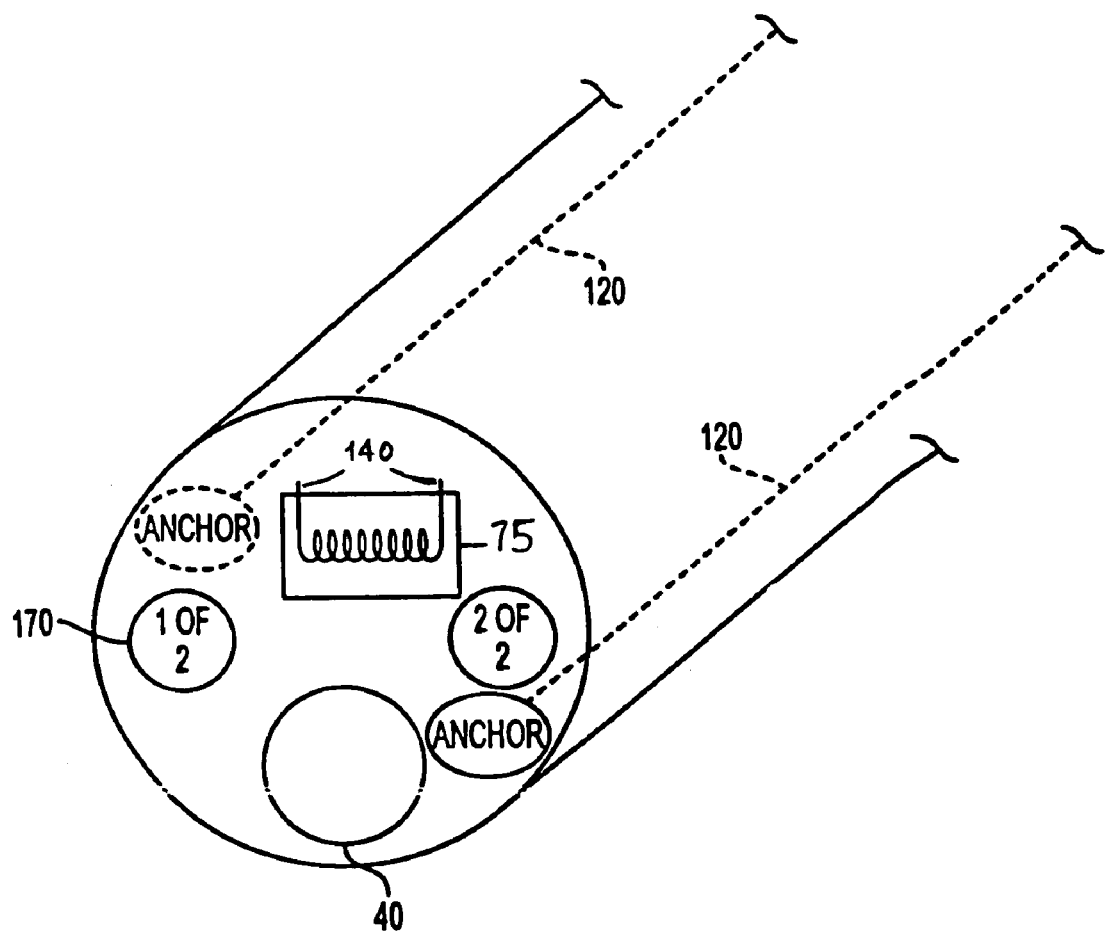
FIG. 4 is a cross-section of an endoscope depicting an open lumen (40) for inserting a therapeutic instrument or fluid, an illumination source (e.g., a light fiber or white LED)(170), tensile members (120) or a CCD (70).

I. Endoscopes having at Least Multifunctional Wires Transmitting Power to More than One Element The endoscopes of this invention may comprise wires that transmit power to an electronic chip and to a light in the endoscope. In particular, the endoscope has a proximal portion (10) and a distal portion (20) wherein the distal portion (20) of the endoscope comprises (a), (b) and (c) wherein, (a) is a tube (30) having a distal end (50) and a proximal end (60) with an open lumen (40) which may be filled partially or completely with a compressive load bearing material wherein the tube has an outer shielding layer, an inner compressive layer and a middle conductive layer, wherein one or more tensile members are positioned within the compressive layer and extend from the distal end to the proximal end of the tube, (b) is an electronic chip (70) positioned at the distal end (50) of the tube wherein the electronic chip (70) is electronically connected to the conductive layer, and (c) is a lens (80) positioned at the distal end (50) of the tube and disposed adjacent to the electronic chip (70), and wherein the electronic chip (70) is connected to one or more wires (140) wherein the one or more wires transmit current from a power connection 180 to the electronic chip in addition to transmitting current to a light 75 within the endoscope. See, e.g., FIGS. 1B and 4. The wires may be made of e.g., copper, BeCu, or copper-coated steel, and be electronically connected to the electronic chip and to the light (75) in the endoscope. wherein the electronic chip (70) is connected to one or more wires (140) wherein the one or more wires transmit current to the electronic chip in addition to transmitting current to a light within the endoscope. See, e.g., FIG. 4. The wires may be made of e.g., copper, BeCu, or copper-coated steel, and be electronically connected to the electronic chip and to the light in the endoscope.

The endoscopes described herein with or without a lumen filled with a compressive load bearing material may further comprise a multifunctional component wherein the multifunctional component may be one or more of (d), (e) or (f) wherein:

(d) is a video circuit wherein the video circuit
 (i) transmits a video signal and serves as a tensile member; or
 (ii) transmits a video signal and transmits current to the electronic chip;
(e) is a outer shielding layer providing
 (i) protection and a substrate for a signal trace; or
 (ii) protection and EMI shielding; or
 (iii) protection and transmission of light; and
(f) is a tensile member providing
 (i) steering and transmission of a video signal; or
 (ii) steering and transmission of current to a light within the endoscope; or
 (iii) steering and transmission of light.

II. Endoscopes having Tensile Members Embedded within an Inner Layer of Compressive Material The endoscopes of this invention may have a proximal portion (10) and a distal portion (20) wherein the distal portion (20) comprises (a), (b) and (c) wherein, (a) is a tube (30) having a distal end (50) and a proximal end (60) with an open lumen (40), filled partially or completely with a compressive load bearing material, wherein the tube (30) has an outer shielding layer (90), and a middle conductive layer (110), wherein one or more tensile members (120) are positioned within the compressive layer and extend from the distal end to the proximal end of the tube, (b) is an electronic chip (70) positioned at the distal end (50) of the tube (30) wherein the electronic chip (70) is electronically connected to the conductive layer, and (c) is a lens positioned at the distal end of the tube and connected to the electronic chip; wherein this endoscope, having a lumen filled partially or completely with a compressive load bearing material, may comprise a multifunctional component which may be one or more of (d), (e) or (f) wherein:

(d) is a video circuit wherein the video circuit
 (i) transmits a video signal and serves as a tensile member or
 (ii) transmits a video signal and transmits current to the electronic chip;
(e) is an outer shielding layer providing
 (i) protection and a substrate for a signal trace,
 (ii) protection and EMI shielding or
 (iii) protection and transmission of light; or
(f) is a tensile member providing
 (i) steering and transmission of a video signal,
 (ii) steering and transmission of current to a light within the endoscope, or
 (iii) steering and transmission of light.

III. Endoscopes having at least an Inner Compressive Load Bearing and Light Transmitting Layer The endoscopes of this invention may have a compressive material that transmits light and fills or partially fills the endoscope lumen. In particular, the endoscopes may have a proximal portion (10) and a distal portion (20) wherein the distal portion comprises (a), (b) and (c) wherein:

(a) is a tube (30) having a distal end (50) and a proximal end (60) with an open lumen (40), filled partially or completely with a compressive material. The tube may have an outer shielding layer (90), an inner compressive layer and a middle conductive layer (110), wherein one or more tensile members (120) extend from the distal end to the proximal end of the tube maybe positioned within the compressive material within the lumen;

(b) is an electronic chip (70) positioned at the distal end of the tube (30) wherein the electronic chip is electronically connected to the conductive layer, and;

(c) is a lens (80) positioned at the distal end of the tube and connected to the electronic chip, and wherein the compressive material within the lumen is made of a material that is both a compressive load bearing material and a light transmitting material.

The compressive material may be any compressive material that is capable of load bearing and capable of transmitting light, preferably acrylic or polycarbonate. The endoscope may also comprise at least one other component that is a multifunctional component. The multifunctional component may be one or more of (d), (e), (f) or (g), wherein e.g.:

(d) is one or mores wires (140) attached to die electronic chip wherein the wires transmit current to the chip and transmit current to a light source 75 within the endoscope;

(e) is a video circuit wherein the video circuit
  (i) transmits a video signal and serves as a tensile member or
  (ii) transmits a video signal and transmits current to the electronic chip;

(f) is an outer shielding layer providing,
  (i) protection and a substrate for a signal trace,
  (ii) protection and electromagnetic interference (EMI) shielding or
  (iii) protection and transmission of light; or (g) is a tensile member provides
  (i) steering and transmission of a video signal,
  (ii) steering and transmission of current to a light within the endoscope, or
  (iii) steering and transmission of light.

IV. Endoscopes having at least a Multifunctional Video Circuit

The endoscopes of this invention may comprise a video circuit. In particular, the endoscopes of this invention may have a proximal portion (10) and a distal portion (20) wherein the distal portion (20) of the endoscope comprises (a), (b), (c) and (d), wherein (a) is a tube (30) having a distal end (50) and a proximal end (60) with an open lumen (40) wherein the tube has an outer shielding layer (90), an inner compressive layer (100) and a middle conductive layer (110), wherein one or more tensile members (120) are positioned within the compressive layer and extend from the distal end to the proximal end of the tube, (b) is an electronic chip (70) positioned at the distal end of the tube wherein the electronic chip is electronically connected to the conductive layer, (c) is a lens (80) positioned at the distal end of the tube and connected to the electronic chip, and (d) is a video circuit that transmits a video signal and also electronically connects the electronic chip to the conductive layer.

The endoscope may further comprise a multifunctional component which may be one or more of (e) or (f):

(e) an outer shielding layer, wherein the outer shielding layer provides
  (i) protection and serves as a substrate for a signal trace,
  (ii) protection and EMI shielding or
  (iii) protection and transmits light; and (f) one or more tensile members, wherein the tensile member provides
  (i) steering and transmission of a video signal,
  (ii) steering and transmission of current to a light within the endoscope, or
  (iii) steering and transmission of light.

V. Endoscopes having at least a Multifunctional Outer Shielding Layer

The endoscopes of this invention may comprise a multifunctional outer shielding layer. In particular, the endoscopes of this invention have a proximal portion (10) and a distal portion (20) wherein the distal portion (20) of the endoscope, comprises (a), (b) and (c) wherein, (a) is a tube (30) having a distal end (50) and a proximal end (60) with an open lumen (40) wherein the tube has an outer shielding layer (90), an inner compressive layer (100) and a middle conductive layer (110), wherein one or more tensile members (120) are positioned within the compressive layer (100) and extend from the distal end to the proximal end of the tube, (b) is an electronic chip (70) positioned at the distal end of the tube wherein the electronic chip is electronically connected to the conductive layer, and (c) is a lens (80) positioned at the distal end of the tube and connected to the electronic chip, and wherein the outer shielding layer (90) is a multifunctional component providing:
  (i) protection and serves as a substrate for a signal trace,
  (ii) protection and EMI shielding or
  (iii) protection and transmission of light.

VI. Endoscopes having at least Multifunctional Tensile Members

The endoscopes of this invention may comprise multifunctional tensile members. In particular, the endoscopes of this invention having a proximal portion (10) and a distal portion (20) wherein the distal portion comprises (a), (b) and (c) wherein, (a) is a tube (30) having a distal end (50) and a proximal end (60) with an open lumen (40) wherein the tube has an outer shielding layer (90), an inner compressive layer (100) and a middle conductive layer (110), wherein one or more tensile members (120) are positioned within the compressive layer and extend from the distal end to the proximal end of the tube, (b) is an electronic chip (70) positioned at the distal end (50) of the tube wherein the electronic chip (70) is electronically connected to the conductive layer (110), and (c) is a lens (80) positioned at the distal end (50) of the tube and connected to the electronic chip, wherein the tensile member (120) is a multifunctional component providing:
  (i) steering and transmission of a video signal, or;
  (ii) steering and transmission of current to a light within the endoscope, or
  (iii) steering and transmission of light.

Preferably the tensile member provides steering and transmits current to a light source. The tensile member may be made of copper, BeCu, or steel.

In endoscopes of this invention comprising multifunctional wires, the multifunctional wires may attach the electronic chip to the conductive layer and may be attached to a light source within the endoscope providing current to both the electronic chip and the light source. Such multifunctional wires may be composed of copper or aluminum.

In endoscopes of this invention comprising, multifunctional video circuits, the multifunctional video circuit may be made of e.g., copper, BeCu or copper-coated steel, and also serves as a tensile member directing the movement of the endoscope.

In the endoscopes of this invention comprising a multifunctional outer shielding layer, the multifunctional outer shielding layer may protect the internal components of the endoscope from physical trauma, as well as protect the subject from contacting the internal components, and may also serve as a pathway for a signal or return signal. The multifunctional outer shielding may be made of a material that provides protection from physical trauma and provide EMI. Such materials may be any current carrying metal, e.g., copper or aluminum. Preferably the outer shielding layer is a tubular flex circuit which comprises the endoscope components on its inner surface (see FIG. 1B.)

The multifunctional tensile members may be made of a material suitable for providing both steering and transmission of a video signal. Such materials include, e.g., copper, BeCu or copper-coated steel. Preferably, the tensile members may be connected to the electronic chip and transmit current to the chip.

Preferably, the multifunctional components are tensile members made of a material suitable for providing both steering and transmission of current to a light within the endoscope. Such materials include, e.g., copper, BeCu, or copper-coated steel. The tensile member may be connected to the light and a current source.

The multifunctional components may be tensile members made of a material suitable for providing both steering and transmission of light. Such material includes, e.g., polycarbonate, polymethylmethacrylic, or a composite of a polymer for example, polycarbonate, polymethyl, methacrylic, polyvinylchloride and a stainless steel mesh. The light transmitting material may be surrounded by any material that is used conventionally for tensile members, for example stainless steel.

The compressive load bearing material which partially or completely fills the lumen of the endoscope of this invention is preferably stainless steel and may be in addition to the compressive layer and may be made of the same material as the compressive layer. The lumen may be filled with a load bearing compressive layer, which eliminates the need for an inner compressive layer forming part of the tube.

The outer shielding layer (90) of the endoscope tube may be a polymer for example polyamide or any fluoropolymer such as PTFP, TFE, e.g. polyamide. The middle conductive layer (110) may be a polymer fill, e.g., glass, metal or ceramic fibers and may be co-extruded e.g., as a metal or plastic braid. Glass or ceramic elements would need to be "metal coated glass" or "metal coated ceramic" to make them conductive. Carbon fibers may also be sufficiently conductive. The inner compressive layer (100) may be a lubricious and/or scratch resistant material, e.g., PTFE and its variants, ETFE, TFE, etc.

The endoscope tube (30) may be constructed using flex circuit technology to combine the outer shielding layer and a current carrying component of the endoscope. A flat flex circuit may be rolled up into a tube and sealed, e.g., by seam welding or by interconnecting mechanical tabs. The current carrying components may be positioned within the flex circuit or along the inner surface of the tubular flex circuit and be connected to a power source, an electronic chip and/or a light source.

The lens (80) may be the final optical component in the endoscope tube (30), as viewed distal to proximal (or in direction of light travel; opposite the scope user's perspective). The lens (80) may cover the electronic imaging chip (70), preferably either a CCD (charge coupled device) or a CMOS based chip, which is less costly. Connected to and behind the electronic chip are wires (140) leading away from the chip. Preferably, signal processing components (150) are positioned alongside or immediately behind the chip (70) (FIG. 1), for signal conditioning purposes, e.g., protecting a transmitted signal from various noise sources and interference. The signal processing component may be an amplifier circuit. In the endoscope of this invention, one or more of these components, e.g., the current carrying component, may be formed onto the distal end (50) of the endoscope, or dispersed along the inner radius of the tube, e.g. the inner radius of a coiled up/rolled up flex circuit (160) (FIG. 1). An advantage of forming the components onto the distal tip of the endoscope or dispersing the components along the inner radius of the tube formed from a flex circuit, is the avoidance of noise. Furthermore, this arrangement of the components provides an assembly advantage, allowing for automated equipment to add the components to the endoscope tube. This avoids traditional hand assembly, which typically increases the cost of current endoscopes. The electronic components can be miniaturized and attached to a flex circuit before it is rolled up, either manually or by automated equipment.

A large amount of white light is essential for proper functioning of CCD and other electronic imaging components. This is traditionally provided by a separate light transmission component typically made of bundles of drawn glass, with the individual fibers about 0.001 inches to about 0.002 inches in diameter. The transmission of light may be accomplished by constructing components, which previously did not transmit light through the endoscope, of a light transmitting material. For example, one or more of the outer shielding layer (90), middle compressive layer (100) or inner conductive layer (110) of the tube (30) may be made of a light transmitting material to transmit white light through the tube and from one end of the tube to the other. The tensile members (120) may also be made of a light transmitting material and thus not only steer the endoscope but also provide light. Such light transmitting materials include e.g., acrylic, or polycarbonate.

Current endoscopes may be steered by means of tensile members, which are usually wires extending from the distal to the poximal portion of the endoscope. These wires are usually braided wire rope to increase flexibility. The wires are usually disposed in opposing pairs—pulling on one causes that side of the scope to decrease in length at the distal tip, pulling/steering the device toward that side. Pulling the other wire causes the device to first straighten and then deflect in the opposite direction. Plastic and alternate materials have found little application as control wires or cables because their modulus of elasticity is one or two orders of magnitude less than metals. In the endoscopes of this invention, the mechanical tensile members (120) may be constructed of a material that also serves to carry current. The tensile members (120) may carry current instead of, or in addition to, traces (formed, e.g., by photolithography or other means) on the flex circuit. Materials suitable for current carrying tensile members includes, e.g., copper, BeCu or copper-coated steel. The tensile members may carry current and they may be coated with an extruded or shrink wrap polymer that is common to the wire rope industry, e.g., PTFE, ETFE or nylon.

The tensile members in the endoscopes of this invention may be surrounded by a compression component, e.g., an extension spring (a spring with the coils touching one another) which balances the tensile steering. The compressive load may be shared by one or more of the other endoscope components resulting in compressive layers within the endoscope tube. A material that is suitable for bearing a compressive load is any high modulus material 10,000,000 to 50,000,000 psi, e.g., steel, copper, BeCu, aluminum or tungsten. The compressive load bearing material may be coaxial with the tensile members.

The endoscope tube may also comprise an "objective head" or distal tip component, which holds all of the components discussed supra, e.g., tensile members (120), a component that transmits light, a chip (70) and lens (80) in proper alignment. The objective head may also serve as a lens barrel for the imaging elements, e.g., the chip, the wires, the lens and the component that transmits light, or as a stiff anchoring point for the deflection wires/tensile members (120). This objective head may or may not use a machined component.

The endoscopes of this invention comprise a proximal portion and a distal portion wherein the distal portion comprises a tube having an open lumen and wherein the tube has a distal end and a proximal end, an electronic chip and a lens. Described herein are additional components that have multiple functions, herein referred to as "multifunctional components," and it is envisaged that the endoscopes of this invention may comprise any combination of the multifunctional components described herein.

I claim:

1. An endoscope having a proximal portion and a distal portion, said endoscope comprising:
   a tube having a distal end and a proximal end and having a lumen disposed from said distal end to said proximal end, and said tube also having an outer shielding layer disposed about an outside surface of said tube, an inner compressive layer and a middle conductive layer, said middle conductive layer being disposed between said outer shielding layer and about said inner compressive layer;
   at least one tensile member disposed within said compressive layer, and said tensile member extending from said distal end to said proximal end of said tube;
   an electronic chip positioned at the distal end of said tube, and said electronic chip being electrically connected to said middle conductive layer; and,
   a lens positioned at the distal end of said tube-to be disposed adjacent to the electronic chip,
   wherein said inner compressive layer is a light transmitting material.

2. The endoscope of claim 1 wherein the inner compressive layer is acrylic or polycarbonate.

3. The endoscope of claim 1 wherein the tube further comprises a flex circuit as the outer shielding layer and said flex circuit including a current carrying component providing current to the electronic chip.

4. The endoscope of claim 1 wherein the electronic chip is a charge coupled device or a CMOS based chip.

5. The endoscope of claim 3 wherein said current carrying component is at least one wire that is attached to the electronic chip, and said wire is further disposed to transmit current to said chip and also disposed to transmit current to a light source within the endoscope;
   said electronic chip including a video circuit, said video circuit being disposed to produce an electronic video signal;
   said flex circuit further including a conductive layer and being disposed about said endoscope; and protect at least said middle conductive layer and also said inner compressive layer from mechanical shock forces; and
   said tensile member is disposed to steer said distal portion of said endoscope to point to different directions.

6. The endoscope of claim 5 wherein the wire is copper or aluminum wire.

7. The endoscope of claim 5 wherein said electronic chip includes a layer made of copper or BeCu or copper-coated steel.

8. The endoscope of claim 5 wherein the outer shielding layer includes a current carrying material.

9. The endoscope of claim 8 wherein the current carrying material is copper or aluminum.

10. The endoscope of claim 5 wherein the tensile member is made of copper, BeCu and copper-coated steel.

11. The endoscope of claim 5 wherein the tensile member further provides transmission of light.

12. The endoscope of claim 5, wherein the tube comprises a flex circuit which comprises the outer shielding layer and a current carrying component providing current to the electronic chip.

13. The endoscope of claim 12, wherein said lumen is filled with a load bearing material.

14. The endoscope of claim 1 wherein said electronic chip includes a layer made of polycarbonate, polymethylmethacrylic or polyvinylchioride polymer.

15. The endoscope of claim 1 wherein the lumen is filled with a compressive load bearing material.

16. The endoscope of claim 15 wherein the tube comprises a flex circuit which comprises the outer shielding layer and a current carrying component providing current to the electronic chip.

17. An endoscope having a proximal portion and distal portion, said endoscope comprising:
   a tube having a distal end and a proximal end and having a lumen disposed from said distal end to said proximal end, and said tube also having an outer shielding layer disposed about said tube, an inner compressive layer and a middle conductive layer, at least one tensile member disposed within said compressive layer, and said tensile member extending from said distal end to said proximal end of said tube, said tube further including a flex circuit as the outer shielding layer and said flex circuit including a current carrying component providing current to an electronic chip;
   said electronic chip positioned at the distal end of said tube, and said electronic chip being electrically connected to said middle conductive layer; and,
   a lens positioned at the distal end of a said tube to be disposed adjacent to the electronic chip, wherein said inner compressive layer is a light transmitting material, and said current carrying component is at least one wire that is attached to the electronic chip, and said wire is further disposed to transmit current to said chip and also disposed to transmit current to a light source within the endoscope;
   said electronic chip including a video circuit, said video circuit being disposed to produce an electronic video signal;
   said flex circuit including a conductive layer and being disposed about said endoscope, and
   said tensile member is disposed to steer said distal portion of said endoscope to point to different directions.

18. The endoscope of claim 17 wherein the wire is copper or aluminum wire.

19. The endoscope of claim 17 wherein said electronic chip includes a layer made of copper or BeCu or copper-coated steel.

20. The endoscope of claim 17 wherein the outer shielding layer includes a current carrying material.

21. The endoscope of claim 20 wherein the current carrying material is copper or aluminum.

22. An endoscope having a proximal portion and a distal portion, said endoscope comprising;
   a tube having a distal end and a proximal end and having a lumen disposed from said distal end to said proximal end, a tensile member being situated in said lumen, and said tube also having an outer shielding layer disposed about said tube, an inner compressive layer disposed inside said tube and a middle conductive layer, said middle conductive layer being disposed between said outer shielding layer and about said inner compressive layer, and said tensile member extending from said distal end to said proximal end of said tube;
   an electronic chip positioned at the distal end of said tube, and said electronic chip being electrically connected to said middle conductive layer; and,
   a lens positioned at the distal end of said tube to be disposed adjacent to the electronic chip,
   wherein said inner compressive layer is a light transmitting material.

23. The endoscope of claim 22 wherein the tensile member comprises steel.

* * * * *